United States Patent [19]

Imamura

[11] 4,080,390

[45] Mar. 21, 1978

[54] PROCESS FOR THE PRODUCTION OF O-PHENYLPHENOL

[75] Inventor: Juichi Imamura, Chofu, Japan

[73] Assignee: Director-General of the Agency of Industrial Science and Technology, Tokyo, Japan

[21] Appl. No.: 695,039

[22] Filed: Jun. 11, 1976

[30] Foreign Application Priority Data

Jun. 13, 1975  Japan .................................. 50-71571

[51] Int. Cl.² ............................................. C07C 37/06
[52] U.S. Cl. .................................. 260/620; 252/459; 252/460
[58] Field of Search ................. 260/620; 252/459, 460

[56] References Cited

U.S. PATENT DOCUMENTS

| | | | |
|---|---|---|---|
| 3,580,970 | 5/1971 | Swift | 260/620 |
| 3,697,606 | 10/1972 | Frendawald et al. | 260/620 |
| 3,923,695 | 12/1975 | Weissel et al. | 260/620 |
| 3,932,536 | 1/1976 | Weissel et al. | 260/620 |
| 3,933,924 | 1/1976 | Weissel et al. | 260/620 |
| 3,972,951 | 8/1976 | Kapner et al. | 260/620 |
| 3,980,716 | 9/1976 | Elliot | 260/620 |

FOREIGN PATENT DOCUMENTS 1,543,878  1/1970  Germany ............................ 260/620

*Primary Examiner*—Norman Morgenstern
*Attorney, Agent, or Firm*—William J. Daniel

[57] ABSTRACT

A process for the production of o-phenylphenol in the presence of a catalyst composed of a γ-alumina or silica-alumina support having a BET surface area of 150 – 300 m²/g, a pore capacity of 0.50 – 0.85 ml/g and an iron content of at most 0.1 % by weight in terms of $Fe_2O_3$ and an alumina content of at least 90 %, the support carrying thereon platinum in an amount of 0.1 – 5.0 % by weight based on the support, iridium in an amount of 0.1 – 0.4 times that of the platinum and an alkali metal oxide in an amount of 0.5 – 8.0 % by weight of the support. o-Phenylphenol is prepared at a high selectivity over a long period of time by supplying onto the catalyst maintained at 300° – 420° C o-cyclohexylphenol or a dehydrodimerized condensate obtained by aldol condensation of cyclohexanone together with gaseous hydrogen in an amount per hour in terms of liquid volume of 0.1 – 1.5 times the volume of the catalyst, and elevating the reaction temperature stepwise or continuously with the lapse of the reaction time, while slowing down, if necessary, the rate of supplying the starting materials, to effect a dehydrogenation reaction.

4 Claims, No Drawings

PROCESS FOR THE PRODUCTION OF O-PHENYLPHENOL

BACKGROUND OF THE INVENTION

The present invention relates to a process for producing o-phenylphenol in a good yield for a long period of time wherein o-cyclohexylphenol or a dehydrodimerized condensate obtained by aldol condensation of cyclohexanone is dehydrogenated in the presence of a new catalyst.

o-Phenylphenol is an industrial chemical finding a wide variety of applications as dye intermediate products, photographic chemicals, additives in rubber industry and bactericides of low toxicity.

We had made various researches on ways for synthesizing o-phenylphenol by dehydrogenation and, as the result, found that o-phenylphenol can selectively be synthesized by subjecting o-cyclohexylphenol or a dimer obtained by aldol condensation of cyclohexanone to a catalytic dehydrogenation reaction in vapor phase in the presence of a catalyst composed of an alumina support or a silica-alumina support of a high alumina content having carried thereon palladium or platinum in metallic form and an appropriate amount of an alkali (Japanese Patent Provisional Publn. No. 13267/ 71). However, this process was not satisfactory for producing o-phenylphenol at a high selectivity because it is subject, depending upon the kind of catalyst, to rapid and considerable reduction in selectivity with the lapse of time, thus shortening the life span of the catalyst. Accordingly, we continued researches for developing a catalyst of a long life utilizable for producing o-phenylphenol, particularly a new platinum catalyst which is free of iridium and uses an active alumina support. However, we found it difficult to produce catalysts having the same activity and the same life span and failed to provide catalysts which are stable in selectivity for a long period of time.

As a result of further researches made to overcome the drawbacks of the prior processes, we have developed a process wherein a catalyst composed of a support of specific nature having carried thereon platinum as main catalyst component and iridium and an alkali metal as co-catalyst components is used for the production of o-phenylphenol.

BRIEF SUMMARY OF THE INVENTION

Accordingly, the present invention provides a process for the production of o-phenylphenol, characterized by supplying onto a catalyst maintained at 300°–420° C o-cyclohexylphenol or a dehydrodimerized condensate obtained by aldol condensation of cyclohexanone together with gaseous hydrogen in an amount per hour in terms of liquid volume of 0.1–1.5 times the volume of the catalyst, and elevating the reaction temperature and/or slowing down the rate of supplying the starting materials to effect a dehydrogenation reaction. The catalyst is composed of a γ-alumina support having an iron content of at most 0.1% by weight in terms of $Fe_2O_3$, a BET surface area of 150–300 m$^2$/g and a pore capacity of 0.50–0.85 ml/g or a silica-alumina support having an alumina content of at least 90% in addition to the above defined iron content, BET surface area and pore capacity, which support carries thereon platinum in an amount of 0.1–5.0% by weight of the support, iridium in an amount of 0.1–0.4 times the amount the platinum and an alkali metal oxide in an amount corresponding to 0.5–8.0% by weight of the support.

It is an object of the present invention to provide a process for producing o-phenylphenol at a high selectivity by dehydrogenation for a long period of time.

Another object of the present invention is to provide a process for producing o-phenylphenol at a high selectivity for a long period of time in the presence of a new catalyst which is high in activity and has a long life.

Still another object of the present invention is to provide a new catalyst suitable for producing o-phenylphenol at a high selectivity by dehydrogenation for a longer period of time.

DETAILED DESCRIPTION OF THE INVENTION

The support for the catalyst utilizable in the process of this invention is γ-alumina having a BET surface area of 150–300 m$^2$/g and a pore capacity of 0.50–0.85 ml/g or silica-alumina having an alumina content of at least 90% and the same BET surface area and pore capacity. In addition, the support is characterized by a low iron content of at most 0.1% by weight in terms of $Fe_2O_3$. In view of the chemical composition of the raw materials, these supports are usually and inevitably contaminated with a small amount of iron. Hitherto, contamination with iron has been permitted in the art of the assumption that it did not affect the selectivity to o-phenylphenol. As a result of various researches on the effect of iron, it has now been found that in the production of o-phenylphenol by dehydrogenation, iron contamination has no influence upon the catalytic activity for a short period of time but considerably reduces the selectivity to o-phenylphenol in the dehydrogenation reaction carried out over a relatively long period of time. It is necessary, therefore, to limit the iron content in the support of the present invention to at most 0.1% by weight in terms of $Fe_2O_3$.

It is a matter of course that contamination of the support with arsenic, lead, mercury, copper and the like should be prevented because these metals possess, as widely known, a strong poisoning action to platinum catalyst systems as contemplated in the present invention. Existence of sulfate iron in an amount of less than about 3% by weight and $Na_2O$ in an amount less than about 0.1% by weight has no influence on the activity to the dehydrogenation reaction of this invention or on catalyst life. Existence of a small amount of silica of course has no influence on the activity and life of the catalyst.

The catalyst components are provided on the support usually in the following manner: Given amounts of platinum and iridium are carried in the form of water-soluble salts on the support and sufficiently reduced with hydrogen at 350°–400° C whereby the catalyst components are carried in metallic form on the support which is then treated according to a soaking method to add an oxide of sodium or potassium to the support. The treatment for baking and reduction with hydrogen is satisfactorily carried out for 2–3 hours.

The amount of platinum incorporated into the catalyst of the present invention varies according to the sorts of carrier, the amount of an alkali added and the reaction conditions such as the reaction temperature and the rate of supplying the starting material, but is preferably within a range of 1–5.0% by weight, particularly 0.5–3.0% by weight based on the support for achieving high activity, high selectivity and long life. If the amount is too small, all of the activity, selectivity and life of the catalyst is badly affected. On the other hand, if the amount of excessively larger, no considerable negative effect will result but some undesirable phenomena may occur such as excessive rate of reaction and activation of side reactions. Contrariwise, no particular advantage is obtained by using an excess amount of platinum. An amount of platinum exceeding 5% by weight is not preferably also from an economical point of view. Catalyst life is significantly influenced by the amount of platinum and is prolonged, depending on the kind of support, by merely increasing the amount of platinum incorporated into the catalyst. Such effect becomes notable when the amount of platinum incorporated is at leat 2.0% by weight. Depending on the kind of support, therefore, an amount of platinum incorporated within a range of 2.0–4.0% by weight is especially preferable.

The optimum amount of iridium incorporated into the catalyst is also variable more or less depending upon the kind of support and other factors in the reaction but is generally about 0.1–0.4 times the weight of platinum. Care should be taken in choosing the amount of iridium because the effect will be reduced if the amount is too small and because activity to dehydrogenation and selectivity will be reduced if the amount is excessively large. For example, the use of a catalyst wherein the amount of platinum incorporated is 0.5% by weight and the amount of iridium incorporated is 2.0% by weight based on the platinum afforded a reaction rate of 100%, a dehydrogenation rate of 73% and a selectivity to o-phenylphenol of 57%, while the use of a catalyst wherein the amount of platinum incorporated is 1.0% by weight and the amount of iridium incorporated is 0.2% by weight based on the platinum afforded under the same reaction condition as above a reaction rate of 100%, a dehydrogenation rate of 98% and a selectivity to o-phenylphenol of 94%. In case iridium is not used as a co-catalyst component but as a main catalyst component, selectivity to o-phenylphenol is low and activity to dehydrogenation is also relatively low as compared with the case of using a platinum catalyst. Accordingly, it is quite surprising that if a small amount of iridium is added as a co-catalyst component to a platinum catalyst, the resultant catalyst maintains high level of activity and selectivity for a long period of time as compared with the case whein iridium is not added. As the reduction in activity to dehydrogenation and in selectivity to o-phenylphenol of the platinum catalyst is prevented by the co-catalyst action of iridium, the catalyst life is significantly prolonged.

An oxide of sodium or potassium is preferably added in the form of a carbonate or hydroxide thereof. Sodium or potassium may be added in the form of another salt such as nitrate or acetate, provided it can be converted into an oxide and can show alkalinity on the catalyst. Such alkali is preferably added in the form of an oxide thereof in an amount of 0.5–8.0% by weight based on the support. If the amount is too small, the co-catalytic effect is not satisfactorily exhibited. On the other hand, if the amount is excessively large, activity to dehydrogenation of the catalyst is reduced. The optimum amount of the alkali added varies with various factors in the reaction such as the reaction conditions and the type of support but is generally within a range of about 2.0–5.0% by weight when the amount of platinum added is 0.5–1.0% by weight, to achieve high activity, high selectivity and long life. Thus, the optimum amount of the alkali is adequately determined within the above mentioned range, taking the various factors into consideration.

The process of the present invention is carried out by maintaining the catalyst of the above composition at a given temperature and bringing o-cyclohexylphenol or a dehydrodimerized condensate obtained by aldol condensation of cyclohexanone into contact with the catalyst. In the latter case, the dehydrodimerized condensate obtained by aldol condensation of cyclohexanone means 2-(1-cyclohexen-1-yl)-cyclohexanone and 2-cyclohexylidene-cyclohexane.

A reaction temperature within a range of 300°–420° C is necessary for producing o-phenylphenol at a high selectivity for a long period of time. Although it is possible, depending on the reaction conditions, to produce o-phenylphenol at a high selectivity even at a reaction temperature higher or lower than this range, the reaction is preferably carried out at a temperature within the above defined range in view of producibility and catalyst life. The optimum reaction temperature varies with the rate of supplying the starting material, the kind and the condition of catalyst used and so is determined properly within the above defined range, taking these various factors into consideration. In general, the use of a higher reaction temperature is desirable when the reaction is conducted at a shorter contact time or when the catalyst is the one that has already been used for a long period of time, but the use of a lower reaction temperature is desirable when the reaction is conducted for a longer contact time or when the catalyst, is a freshly prepared one. In case a freshly prepared catalyst is used and the reaction is conducted over a longer contact time, care should be taken in the selection of the reaction temperature since o-phenylphenol once formed will further be converted at a reaction temperature near 400° C into biphenyl and dibenzofuran.

The rate of supplying the starting material during the dehydrogenation reaction of this invention varies according to various factors in the reaction such as the reaction temperature and the kind and condition of the catalyst, but generally the starting material is preferably supplied in an amount per hour in terms of liquid volume at 60° C of 0.1–1.5 times, preferably 0.2–0.7 times the volume of the catalyst. In this case, the catalyst life was often prolonged by using as a carrier gas hydrogen in a molar proportion of about 0.5–5 times as much as the starting material. As the influence of the rate of supplying the starting material on the catalyst life is particularly significant, care should be taken to conduct the reaction under proper conditions. Otherwise, the catalyst life will considerably be shortened. For example, the use of a freshly prepared catalyst at a higher reaction temperature enables the production of o-phenylphenol at a high selectively even if the rate of supplying the starting material exceeds the above defined range. Under such conditions, however, the catalyst is rapidly deteriorated. From comparison of the quantity of o-phenylphenol produced for a given amount of the catalyst, it has been found that the better result is obtained by supplying the starting material at a rate within the above defined range. In the case of a catalyst used for a long period of time, o-phenylphenol is produced at a high yield by conducting the reaction at a higher temperature even in the event that the rate of supplying the starting material is near the upper limit of the above defined range. However, catalyst life is shortened under such conditions. To maximize the quantity of o-phenylphenol produced by a given amount of the catalyst which has already been used for a long period of time, it is necessary to limit the rate of supplying the starting material to less than the middle value of the above defined range.

As is evident from the above conclusions, the most effective method of using the catalyst is to conduct the reaction initially at a relatively low reaction temperature and at a relatively high rate of supply of the starting material and then at the highest temperature within the above defined range and at the lowest rate of supply of the starting material within the above defined range and then to effect regeneration of the catalyst at that stage.

The regeneration of the catalyst can easily be carried out according to any of the method known among those skilled in the art, for example, by oxidizing the catalyst with a mixed gas of air and nitrogen at a temperature of 300°–400° C, with careful attention lest the temperature exceed the defined range, and thereafter reducing the catalyst with hydrogen at a temperature of 300°–350° C.

The following examples are included merely to aid in the understanding of the invention, and variations and modification may be made by anyone skilled in the art without departing from the spirit and scope of the present invention.

EXAMPLE 1

γ-Alumina pellets (manufactured by Shokubai Kasei Kogyo, Japan; molded alumina pellets having a diameter of 1.5 mm, a length of 3–5 mm, a BET suface area of 226 m$^2$/g, a pore capacity of 0.85 ml/g and an iron content of 0.04% by weight in terms of $Fe_2O_3$) were baked at 580°–600° C for 10 hours while passing air therethrough at a flow rate of 5 liters/hour to prepare an alumina support. To 20.6 g of this catalyst support was added a solution of 0.547 g of $H_2PtCl_6 \cdot 6H_2O$ and 0.074 of $IrCl_4 \cdot H_2O$ in 50 ml of distilled water. By the soaking method, platinum and iridium were uniformly deposited on the support. This catalyst was dried in an electric drier at 110° C, then baked in a catalyst-baking tube (made of Pyrex glass) at 350° C for 3 hours while passing nitrogen therethrough at a flow rate of about 3 liters/hour, and finally reduced with hydrogen at 350°–360° C for 8 hours while passing hydrogen through the tube at the almost same flow rate as above. To this catalyst (21.0 g) was added a soluton of 1.2 g of a commercially available special grade caustic potash in 40 ml of distilled water. By the soaking method, the caustic potash was deposited on the catalyst. This catalyst was dried in an electric drier and then baked at 350° C for 2 hours in a stream of nitrogen to prepare a catalyst for dehydrogenation.

In a catalyst-filling portion of a molybdenum glass reaction tube of 22 mm in inner diameter and 800 mm in length were placed 30 ml (17.5 g) of this catalyst (1.0 wt% Pt — 0.2 wt% Ir — 5 wt% KOH — γ-alumina). The reaction tube was placed in a tubular electric furnace and a dehydrogenation reaction of o-cyclohexylphenol was carried out according to a usual flowing method. Namely, o-cyclohexylphenol maintained at 60° C was fed to the reaction tube at a flow rate of 9 ml/hour by means of a metering pump mounted in a constant temperature bath kept at 60° C and at the same time hydrogen was supplied onto the catalyst at a flow rate of 3 liters/hour. The temperature of the reaction furnace was maintained at 350° C. (In this case, the lowest temperature of the catalyst bed was 325°–327° C durung the reaction.) The resultant product was collected in a product-collecting trap heated with a ribbon heater, taken out occasionally by means of a drawing cock and analyzed according to gas chromatography at elevated temperature using a column of 5 m in lenght and 3% silicone XE-60-chromosolve WAW (silane treated product) as filler.

Investigation of changes in composition of the resulting liquid product with the lapse of reaction time revealed that the reaction rate was at least 93% and the selectivity to o-phenylphenol was at least 95 mole % until 150 hours had elapsed from the initiation of the reaction with a gradual reduction in the reaction rate thereafter. The reaction temperature was adequately elevated to keep the reaction rate at 90% or more. As a result of this adjustment, the reaction temperature was elevated at 402° C after the lapse of 2000 hours from the initiation of the reaction. At this stage, the reaction rate was 95% and the selectivity to o-phenylphenol was 94 mol %.

For the purpose of comparison, a similar experiment was carried out by using the same apparatus and catalyst components as described above in the same manner as described above except that alumina spheres having an iron content of 0.61% by weight in terms of $Fe_2O_3$ ("Neobead" C-4 manufactured by Mizusawa Kagaku, Japan) were crushed to have a size of 12–16 mesh and used as a binder in lieu of γ-alumina described above. In this case, the reaction rate was 38% and the selectivity to o-phenylphenol was 86 mol % at the time of 2 hours after the initiation of the reaction. When the reaction temperature was raised to 390° C, the reaction rate and the selectivity to o-phenylphenol were increased to 82% and 89 mol %, respectively. After passage of 100 hours, however, the reaction rate and the selectivity to o-phenylphenol were reduced to 76% and 81 mol %, respectively, even in the case of elevating the reaction temperature to 410° C. The reaction rate and the selectivity to o-phenylphenol at the time of 200 hours after the initiation of the reaction were 65% and 76 mol %, respectively. After 100 hours from the initiation of the reaction, increase in the reaction rate was hardly recognized and the selectivity to o-phenylphenol rather tended to decrease even when the reaction temperature was further elevated. Thus, elevation of the reaction temperature was not found to be contributive to increase in the yield of the product.

For the purpose of further comparison, a similar experiment was carried out in the same manner as described above except that iridium was excluded from the catalyst. In this comparative experiment, the reaction rate and the selectivity were almost equal to those in the case of incorporating iridium into the catalyst until about 50 hours had elapsed from the initiation of the reaction. Thereafter, however, catalytic activity was rapidly reduced so that o-phenylphenol of high purity could not be obtained even by elevating the reaction temperature or slowing down the rate of supplying the starting material. Although the reaction temperature and the rate of supplying the starting material were adjusted to 375° C and 6.5 ml/hour, respectively, at the time of 250 hour after the initiation of the reaction, the reaction rate and the selectivity to o-phenylphenol were only 88% and 93 mol %, respectively. Although the reaction temperature was raised up to 420° C at the time of 400 hours after the initiation of the reaction, the reaction rate was at most 75%.

EXAMPLE 2

Using Sumitomo active alumina KHA (spherical particles of 2-4 mm in diameter having a BET surface area of 150-180 m$^2$/g, a pore capacity of 0.5-0.6 ml/g and an iron content of 0.03% by weight in terms of Fe$_2$O$_3$) as support, a 2.0 wt% Pt—0.3 wt% Ir—7 wt% Na$_2$CO$_3$ —active alumina catalyst was prepared in the same manner as described in Example 1. (In this case, Na$_2$CO$_3$ was supposed to be converted into Na$_2$O during the treatments for baking and reduction). Using this catalyst, a dehydrogenation reaction of o-cyclohexylphenol was carried out under the same conditions as described in Example 1 whereby changes in the reaction temperature (the maximum and minimum temperatures), the reaction rate and the selectivity with the lapse of time were as tabulated below.

| Lapse of time after the initiation of the reaction (Hrs) | Reaction temperature (° C) (minimum–maximum) | Reaction rate (%) | Selectivity (mol %) |
| --- | --- | --- | --- |
| 100 | 328 – 350 | 98 | 96 |
| 200 | 339 – 360 | 98 | 96 |
| 400 | 354 – 372 | 97 | 93 |
| 700 | 386 – 405 | 98 | 92 |

For the purpose of comparison, a similar experiment was carried out under the same conditions as described in this example except that Neobead C-4 was crashed to have a size of 12-16 mesh and used as support for the catalyst in place of the above mentioned Sumitomo active alumina KHA and that the reaction temperature was 380° C. In this comparative experiment the reaction rate and the selectivity to o-phenylphenol just after the initiation of the reaction were 97% and 86 mol %, respectively. After the lapse of 100 hours from the initiation of the reaction, however, the reaction rate and the selectivity to o-phenylphenol at a reaction temperature of 400° C were reduced to 78% and 85 mol %, respectively.

EXAMPLE 3

An alumina support containing a small amount of silica (manufactured by Shokubai Kasei Kogyo, Japan; a molded product of 1.5 mm in diameter and 3-5 mm in length having a silica content of 2.29% by weight, a BET surface area of 279 m$^2$/g, a pore capacity of a 71 ml/g and an iron content of 0.1% by weight in terms of Fe$_2$O$_3$) was baked for 10 hours at 585°-605° C in a stream of air fed at a flow rate of 3 liters/hour. Using this support, a 0.6 wt%Pt—0.2 wt%Ir—3 wt%K$_2$CO$_3$ —alumina catalyst was prepared in the same manner as described in Example 1. Using 30 ml of this catalyst in an apparatus similar to that described in Example 1, the temperature of the reaction furnace was controlled at 350° C (the minimum temperature in the catalyst layer just after the initiation of the experiment was 316° C) and a dimerized condensate of cyclohexanone was added dropwise at a rate of 12 ml/hour from a microfeeder and at the same time hydrogen was supplied at a flow rate of 2 liters/hour. The product was analyzed in the same manner as described in Example 1 whereby the reaction rate and the selectivity to o-phenylphenol at the time of 50 hours after the initiation of the reaction were 100% and 91 mol %, respectively. After the lapse of 50 hours from the initiation of the reaction, only the rate of supplying the starting material was slowed down to 8 ml/hour and the reaction was continued for further 150 hours. After 200 hours from the initiation of the reaction, the reaction rate and the selectivity to o-phenylphenol were 100% and 88 mol %, respectively. At this point, the temperature of the reaction furnace was elevated by 5° C at a time interval of 72 hours and the reaction was continuously carried out. When 600 hours has passed after the initiation of the reaction, the reaction rate and the selectivity to o-phenylphenol were 100% and 90 mol %, respectively.

For the purpose of comparison, a catalyst was prepared from Neobead C-4 crashed to have a size of 12-16 mesh in place of the above mentioned alumina catalyst and a life test of the catalyst was carried out under the same conditions as described above. In this test, the reaction rate and the selectivity to o-phenylphenol were 100% and 61 mol % just after the initiation of the reaction and 100% and 32 mol %, respectively, after a lapse of 20 hours.

EXAMPLE 4

A given amount of alumina sol manufactured by Nissan Kagaku (alumina content: 99.8 wt%) and a given amount of silica sol (trade name "Snowtex" having a silica content of 20.9 wt%) were mixed. The mixture was well stirred in a water bath to evaporate moisture contained therein whereby a silica-alumina having a composition of silica: alumina = 0.8:9.2 was prepared. This was then crushed to have a size of 8-16 mesh and baked for 24 hours at 585°-600° C while passing air through the crashed silica-alumina at a flow rate of 3 liters/hour. Using the resultant product as support, a 4 wt% Pt—1.3 wt%Ir—7 wt%KNO$_3$—silica-alumina catalyst was prepared in the same manner as described in Example 1. Prior to an experiment for dehydrogenation, this catalyst was baked in a stream of nitrogen for 24 hours at 360° C to completely decompose the nitrate residue. This catalyst was found to have a Fe$_2$O$_3$ content of 0.05% by weight.

A dehydrogenation reaction was carried out in the presence of 30 ml of this catalyst by supplying the dimerized condensate and hydrogen at rates of 10 ml/hour and 1 liter/hour, respectively, at 330° C. After 50 hours from the initiation of the reaction, the reaction rate and the selectivity to o-phenylphenol were 100% and 92 mol %, respectively. The reaction was then continued by raising the reaction temperature to 350° C and adjusting the rate of supplying the starting material to 8 ml/hour. At 200 hours after the initiation of the reaction, the reaction rate and the selectivity were 100% and 91 mol %, respectively. When the reaction was further continued for 200 hours by raising the reaction temperature to 370° C, the reaction rate and the selectivity were determined as 99% and 90 mol %, respectively.

For the purpose of comparison, a given amount of an aqueous solution of ferric nitrate was added to a liquid mixture of the above mentioned alumina sol and silica sol so that a support having an iron content of 0.4% by weight in terms of Fe$_2$O$_3$ might be obtained. Using this catalyst, a dehydrogenation reaction was carried out exactly in the same manner as described above. The reaction rate and the selectivity to o-phenylphenol just after the initiation of the reaction were 100% and 53 mol %, respectively. Even in the case of continuing the reaction by raising the reaction temperature to 380° C, the reaction rate and the selectivity after the lapse of 50 hours from the initiation of the reaction were only 100% and 63 mol %, respectively.

EXAMPLE 5

Using the same support as described in Example 4, a 3.5 wt% Pt—1 wt%Ir—10 wt% CH$_3$COONa—Silica—alumina catalyst was prepared in the same manner as described in Example 1. The catalyst was then baked and reduced with hydrogen for the same period of time as described in Example 4. A dehydrogenation reaction was carried out in the presence of 30 ml of this catalyst by supplying o-cyclohexylphenol and hydrogen at rates of 20 ml/hour and 2 liters/hour, respectively, at a reaction furnace temperature of 350° C (the minimum temperature of the catalyst layer during the reaction: 307° C) for 10 hours. The reaction was continued for 250 hours at a rate of supplying the starting material of 10 ml/hour and at a furnace temperature of 360° C and then for 200 hours at a rate of supplying the starting material of 10 ml/hour and at a furnace temperature of 370° C. The reaction was finally continued at a reduced rate of supplying the starting material of 7 ml/hour while elevating the temperature by 5° C at a time interval of 50 hours. Changes in the reaction rate and the selectivity with the lapse of time were as tabulated below.

| Lapse of time after the initiation of the reaction (Hrs) | Reaction rate (%) | Selectivity (mol %) |
|---|---|---|
| 50 | 98 | 95 |
| 250 | 94 | 95 |
| 400 | 92 | 93 |
| 1000 | 93 | 92 |

What is claimed is:

1. A process for the production of o-phenylphenol, characterized by contacting in the presence of hydrogen carrier gas o-cyclohexylphenol or a dehydrodimerized condensate obtained by aldol condensation of cyclohexanone with a catalyst material at 300°–420° C in an amount per hour in terms of liquid volume of 0.1–1.5 times the volume of the catalyst, said catalyst being composed of $\gamma$-alumina or silica-alumina support having a BET surface area of 150–300 m$^2$/g, a pore capacity of 0.50–0.85 ml/g, an iron content of at most 0.1% by weight in terms of Fe$_2$O$_3$ and an alumina content of at least 90%, said support having carried thereon platinum in an amount of 0.1–5.0% by weight based on said support, iridium in an amount of 0.1–0.4 times the amount of platinum, and an alkali metal oxide in an amount of 0.5–8.0% by weight based on said support.

2. A process according to claim 1 wherein the reaction temperature is elevated within a range of 300°–420° C with the lapse of the reaction time.

3. A process according to claim 1 wherein, the rate of supplying the starting material is reduced with the lapse of the reaction time.

4. A process according to claim 1 wherein said alkali metal oxide is an oxide of sodium or potassium.

* * * * *